US00PP33454P2

(12) United States Plant Patent
Shipley et al.

(10) Patent No.: US PP33,454 P2
(45) Date of Patent: Sep. 7, 2021

(54) ***LEUCOPHYLLUM FRUTESCENS* SHRUB NAMED 'SAN ANTONIO ROSE'**

(50) Latin Name: *Leucophyllum frutescens*
Varietal Denomination: San Antonio Rose

(71) Applicants: Nicholas Benoit Shipley, Tucson, AZ (US); Russ Allen Buhrow, Tucson, AZ (US)

(72) Inventors: Nicholas Benoit Shipley, Tucson, AZ (US); Russ Allen Buhrow, Tucson, AZ (US)

( * ) Notice: Subject to any disclaimer, the term of this patent is extended or adjusted under 35 U.S.C. 154(b) by 0 days.

(21) Appl. No.: 16/974,127

(22) Filed: Oct. 14, 2020

(51) Int. Cl.
*A01H 5/00* (2018.01)
*A01H 6/00* (2018.01)

(52) U.S. Cl.
USPC ..... Plt./226

(58) Field of Classification Search
USPC ..... Plt./226
CPC ..... A01H 6/00; A01H 5/00
See application file for complete search history.

*Primary Examiner* — Keith O. Robinson

(57) ABSTRACT

A new and distinct *Leucophyllum frutescens* plant named 'San Antonio Rose' is characterized as a rounded shrub with very large, slightly fragrant, pink flowers, silver/gray leaves and very strong resistance to damping off diseases.

4 Drawing Sheets

Latin name: *Leucophyllum frutescens*.
Varietal denomination: 'San Antonio Rose'.

INTRODUCTION

Shrubs of the genus *Leucophyllum* are commonly called Texas Rangers, simply "Rangers" or barometer plant in English and Cenizo in Mexico. The genus consists of about 12 species native to arid portions of Mexico from Puebla in the south northward to the southern portions of Texas. The various "Rangers" have become popular landscape plants throughout the southwestern United States as well as other areas of the world with similar climates and extending into moister areas successfully as long as the soil has adequate drainage. Seven species of *Leucophyllum* are commonly cultivated, as well as several interspecific hybrid cultivars. The most popularly grown species is *Leucophyllum frutescens*. Several cultivars of this species are grown.

BACKGROUND OF THE INVENTION

The present invention relates to a new and distinct cultivar of *Leucophyllum frutescens*. The cultivar was generated by crossing existing cultivars: 'Green Cloud' X 'Convent'. 'Green Cloud' (not patented) is the female parent and 'Convent' (not patented) is the male parent. Apparently one or both of the above cultivars is heterozygous for many genes, resulting in an $F_1$ population which was quite variable in character. 'San Antonio Rose' is a selection from the $F_1$ generation of this cross and is the object of this application.

SUMMARY OF THE INVENTION

Among the features that distinguish the new *Leucophyllum frutescens* cultivar from all other available and commercial varieties of *Leucophyllum frutescens* known to the inventors are the following combination of characteristics: a shrub with a rounded shape with very large, pink flowers, silver/gray leaves, and very strong resistance to damping off diseases.

The asexual propagation procedure is as follows: Semi-hardwood cuttings 4-5" long are prepared by removing the lower leaves, then dipping the cleared portion of the cut into a 1:10 solution of DIP'N GROW™. The cuttings are then inserted about one inch into prepared peat trays. The trays are moved to a mist house with mist applied every 20 minutes and temperature maintained between 70-85° F. Rooting is generally complete within 4 weeks.

The foregoing characteristics and distinctions come true to form and are established and transmitted through succeeding propagations. The present invention has not been evaluated under all possible environmental conditions, such that the phenotype may vary with variations in environment without a change in the genotype of the plant.

BRIEF DESCRIPTION OF THE DRAWINGS

The accompanying photographs illustrate *Leucophyllum frutescens* 'San Antonio Rose' growing in the ground at a commercial nursery near Sahuarita, Ariz., depicted in color as nearly correct as it is possible to make in a color illustration of the character.

DETAILED PLANT DESCRIPTION

Figure 1:
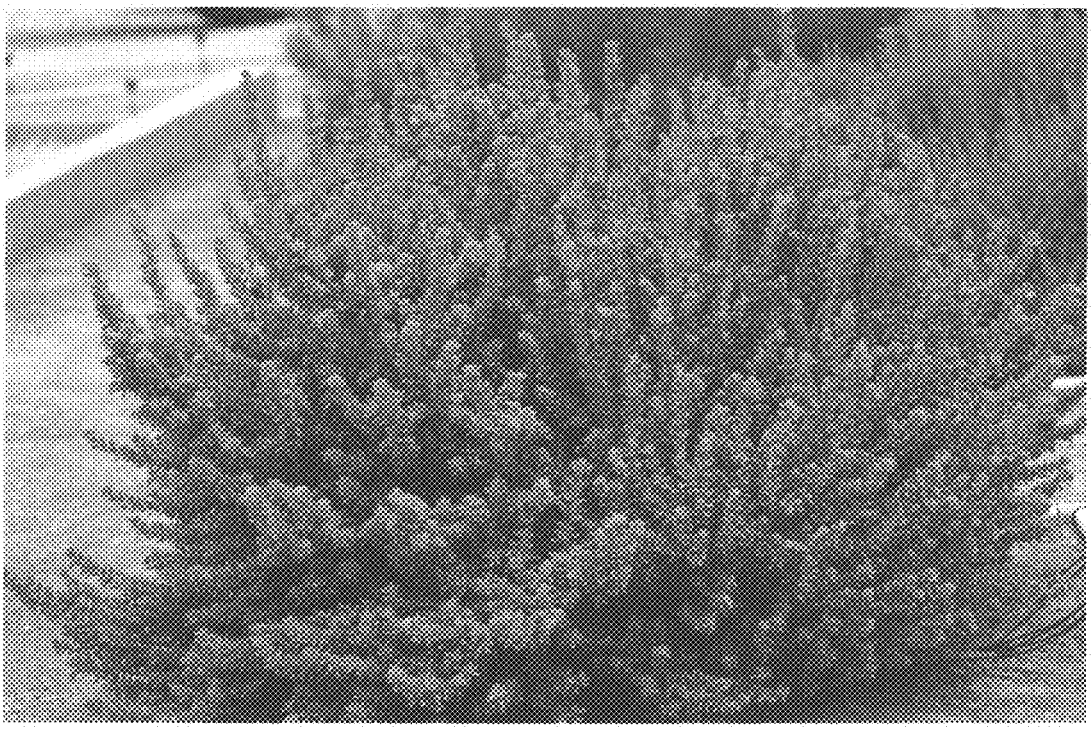
FIG. 1 shows *Leucophyllum frutescens* 'San Antonio Rose' at age 3 years from cutting growing at a commercial nursery near Sahuarita, Ariz.
Figure 2:
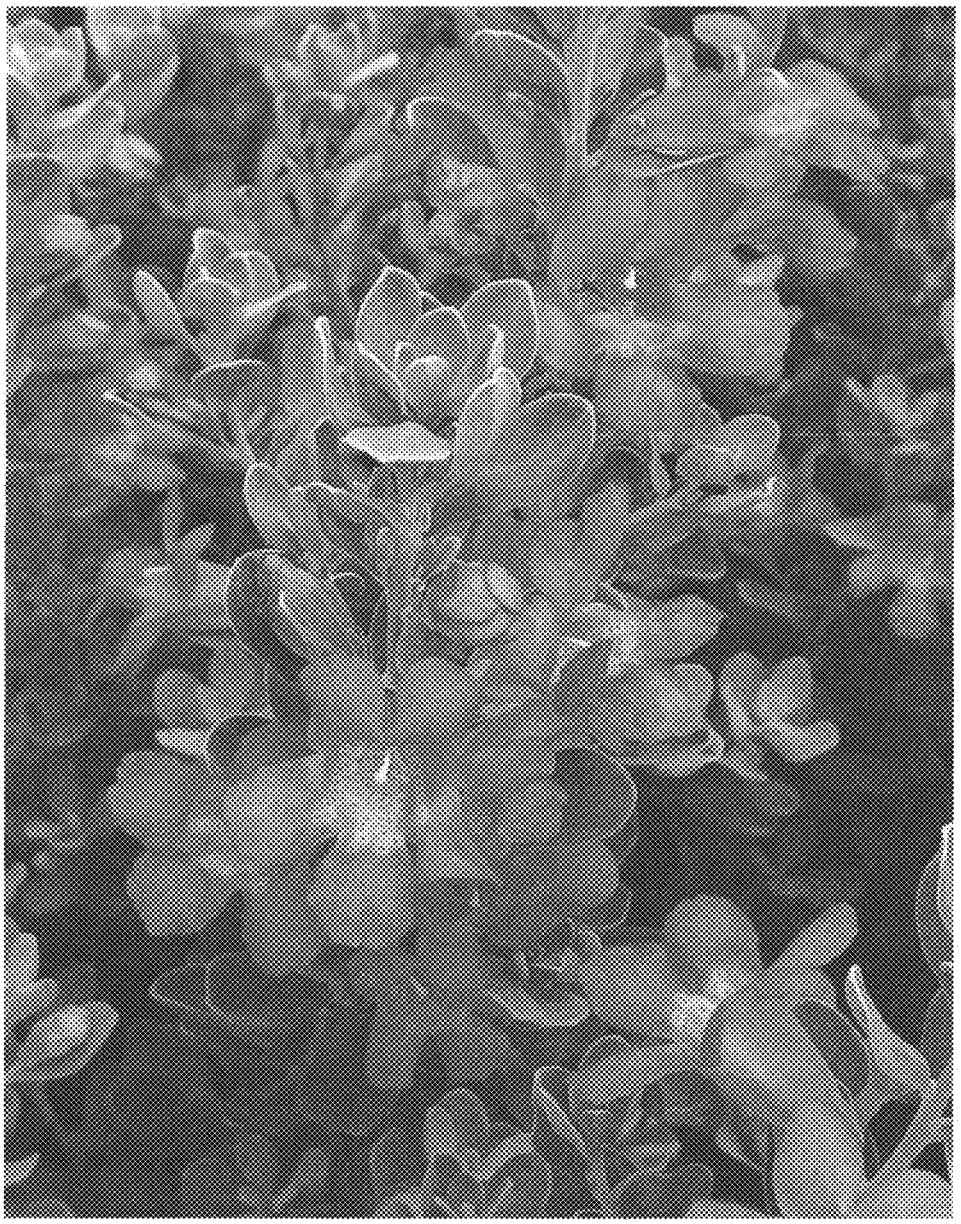
FIG. 2 shows *Leucophyllum frutescens* 'San Antonio Rose' flowers, leaves and young stems.
Figure 3:
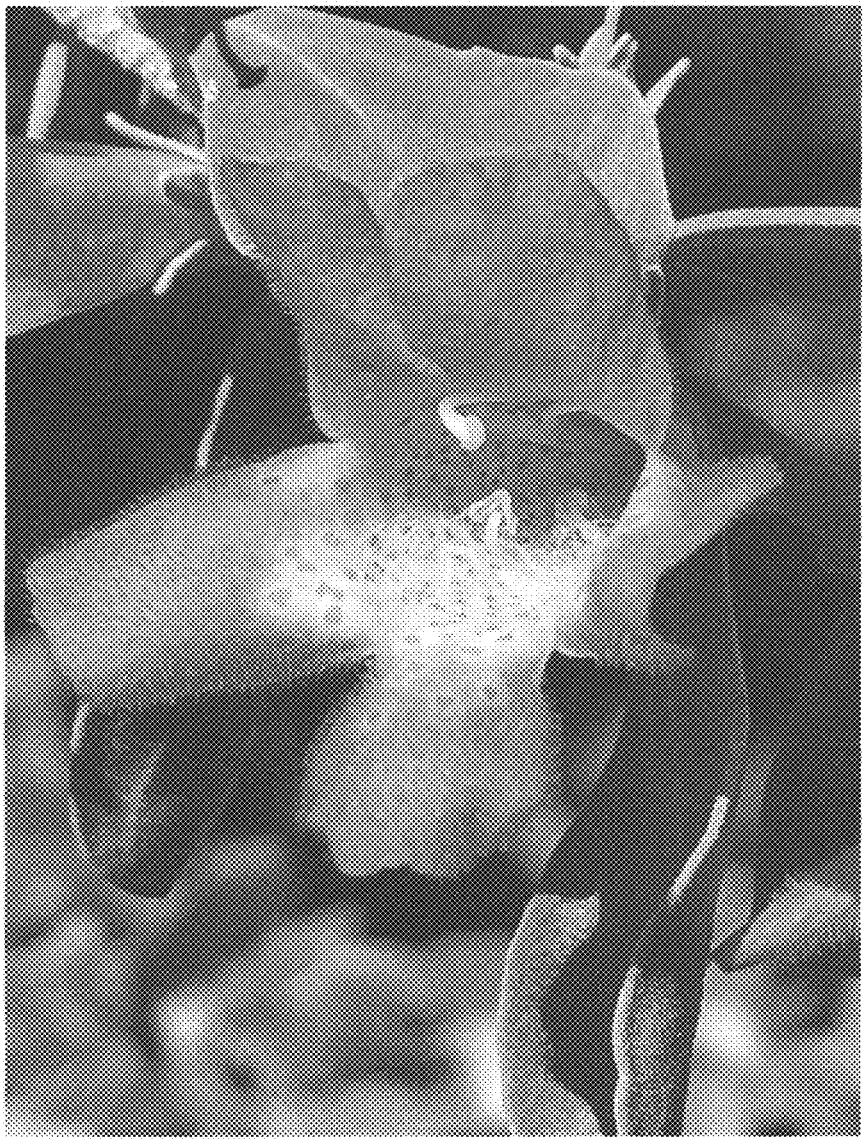
FIG. 3 is a closeup of the flower of *Leucophyllum frutescens* 'San Antonio Rose'.
Figure 4:
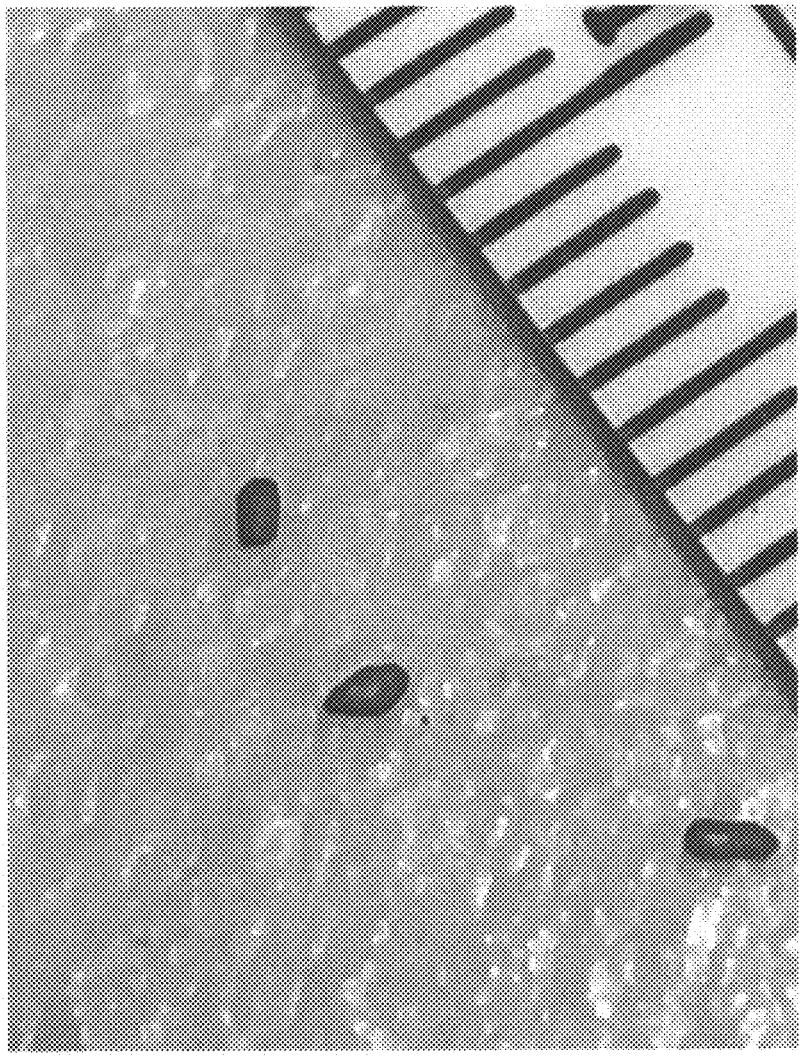
FIG. 4 shows the seeds of *Leucophyllum frutescens* 'San Antonio Rose'. Scale on right in millimeters.

The following is a detailed description of the new *Leucophyllum* plant based upon the original 'San Antonio Rose' plant growing in the ground at a commercial nursery near Sahuarita, Ariz. The color descriptions are based upon the 5th edition R.H.S. Colour Chart, copyright 2007. Color names other than common usage are as listed in *COLOR Universal Language and Dictionary of Names*, by Kenneth L. Kelly and Deane B. Judd; National Bureau of Standards special publication 440. Washington, D.C.: U.S. Department of Commerce, National Bureau of Standards, December 1976.

Plant a much branched shrub with large, showy flowers during the warm season, especially during rainy periods. At age 5 years the plant growing under irrigation in the ground at a commercial nursery near Sahuarita, Ariz. measures about 5 feet tall and 5 feet wide. Measurements and description are based upon this specimen. The general form is loosely spherical.

Young but mature stems are colored 194B, are terete, densely covered with stellate hairs barely identifiable at 10×. Young stems measure from 1.5-2.5 mm in diameter. Older stems, measuring 2.5-5 mm in diameter are colored 197C. By this size/age the stems are striped with glabrous strips alternating with strips covered with stellate hairs which by this time are partially caducous. The glabrous stripes average about 0.5 mm wide, while the pubescent strips are about twice as wide. Branches measuring 5-15 mm in diameter have a netlike pattern of glabrous areas extended axially and colored N77C. Between the smooth areas are lens shaped roughened areas colored closest to 76D. The largest, oldest stems measuring from 2-4 cm in diameter become somewhat furrowed and colored mostly 164D with scattered patches of 202B. The color transition of these areas is rather abrupt. The transition of stem characteristics with stem age is gradual and the specifics of stem diameter characteristics are somewhat variable depending on the vigor and age of a given stem. Branch angle varies from about 30-60°.

The leaf arrangement is alternate. Internodes vary from 1-23 mm in length. Leaves are sessile and slightly narrower than obovate in shape. Leaf bases are acute. Leaves are somewhat coriaceous. Leaves measure from 8-28 mm in length×6-14 mm in width. Leaf size is relatively plastic with growth conditions and stem position. The leaves have pinnate venation, only easily visible on the abaxial surface on mature leaves, typically with 5-7 veins visible. Leaf adaxial surface is finely puberulent with stellate hairs only visible under minimum magnification 10×. Adaxial leaf color is 191A. Leaf abaxial surface is similar to the adaxial surface, but the stellate hairs on this surface are much denser, producing a whiter surface, color 191D.

Axillary buds are obovoid in shape, colored 192C, and densely covered with very fine stellate hairs which require minimum 20× to observe. The axillary buds measure 0.75 mm long×0.5 mm wide.

Flowers are axillary, solitary and concentrated most heavily near the ends of branches.

Pedicels measure 2 mm in length and 1 mm in diameter, terete, color 192A, with dense stellate pubescence.

The flower bud just before anthesis is long obovoid, measuring 17 mm long×6 mm in diameter.

The upper two petal lobes enclose the lower three. The bud apex and adaxial side are colored 63D, the abaxial side is colored 155C. These colors grade into each other along the sides of the bud. The corolla of the unopened bud is glabrous.

Flowers last 1-2 days and are slightly fragrant with a sweet aroma. Flowers measure 20-23 mm long×20-22 mm high×19-24 mm wide.

The flaring calyx is comprised of 5 sepals free to the base, these with a narrowly oblanceolate shape and each measuring 5 mm long×2 mm wide at the widest point. The apex and base are acute in shape. The exterior of the sepals is canescent with stellate hairs and colored 193A. The interior surface is canescent with stellate hairs near the apex and along the margins, Elsewhere the interior surface is covered with scattered, fine hairs, these more or less appressed. The interior sepal surface is colored 138C.

The corolla is fused about ⅔ of the length of the flower, the tube gradually flaring. The tube measures 14-15 mm in length. The upper portion of the tube exterior is colored N74D. The lower portion of the tube exterior is colored 69C. The color grades between these two colors on the sides of the tube exterior. The tube exterior is glabrous.

The corolla has 5 rounded, more or less obovate, petal lobes, the upper two differing from the lower three primarily in the character of the pubescence. The petal lobes measure 9-10 mm long×7-8 mm wide and are spreading and extend forward. The petal lobes are colored 75B abaxially and 75A adaxially. The lower 3 petal lobes are villous adaxially with glandular hairs colored 72B. The upper two petal lobes have identical hairs present, but these hairs are spread sparsely over the adaxial surface except along the margins which are ciliate. A beard of white (NN155D) glandular hairs about 2 mm long extends into the floral tube about 5 mm. Laterally the beard extends from just below the middle of the left lateral petal lobe across the lower portion of the floral tube to just below the middle of the right lateral petal lobe. The floral tube opening at the base of the petal lobes measures 6-7 mm high×8-10 mm wide. The lower ⅔ of the tube interior is colored N155D and dotted with more or less circular spots varying in color from N25A to N25C. These spots measure from 0.25-0.5 mm in diameter. These spots also extend a short distance into the base of the petal lobes. The spots are barely visible on the lower tube exterior. The upper ⅓ of the tube interior is colored 75A. The color changes rather abruptly at the edges of the two different colored portions of the tube. The tube interior is glabrous except for the beard previously noted.

The staminode is absent.

Four epipetalous stamens are present, these attached near the floral tube base. Stamens measure 14-16 mm long×0.5 mm in diameter. The filaments are axially inwardly curved, with filament color NN155B. Anthers are explanate, measuring 2 mm long×0.5 mm wide, anthers and pollen colored 4D.

The pistil measures 16mm long. The ovary has a slightly flattened ovoid shape measuring 2 mm long×1.5 mm wide× 1.25 mm thick, color 154D. The style is slightly curved adaxially along most of its length then rather abruptly near the stigma about 90° from the axis downward into the tube.

Style measures 13 mm long×0.5 mm diameter, terete. The style color is 155B near the base grading to N155B just below the stigma. The stigma is hemidiscoidal, with the hemidisc perpendicular to the main style axis. The hemidisc measures 1.25 mm wide×0.33 mm thick, color 68D. The entire pistil is glabrous.

The ripe fruit is a two celled capsule that dehisces along 4 lines to release the seeds. The fruit measures 4-5 mm long×2.5-3 mm in diameter. The fruit is ovoid in shape before dehiscence. The fruit is glabrous and hard. Mature, but not dry, fruits are colored 138B. Dry, mature fruits are colored N199A. Fruits typically contain about 20 seeds each measuring about 1 mm long×0.5 mm wide. the seeds are smooth and variously shaped due to compression inside the fruit. Seed color is N199C.

*Leucophyllums* are generally insect pest and disease free except for the Texas (Cotton) Root Rot fungus *Phymatotrichum omnivorum* and sudden death in commercial nurseries from damping off.

In heavier soils, especially if the soil becomes waterlogged, damping off can also occur in the landscape. Cultivation of "Rangers" is limited on the eastern margin of the temperature adaptation zone by death because of excessive moisture. Several cultivars including 'Green Cloud' and 'Compacta' are known to have greater than average resistance to damping off diseases. Several cultivars are so sensitive to damping off that they are not economic to produce and are rarely available in the trade. *Leucophyllum frutescens* 'San Antonio Rose' has demonstrated excellent tolerance of high moisture conditions in the nursery with very little loss from damping off. *Leucophyllum frutescens* 'San Antonio Rose' has not been tested for resistance to Texas Root Rot. *Leucophyllum frutescens* 'San Antonio Rose' is hardy to at least 10° F., USDA cold hardiness zone 8.

COMPARISONS TO RELATED *LEUCOPHYLLUM FRUTESCENS* AND *L. FRUTESCENS* HYBRIDS

Compared to its female parent, 'Green Cloud', 'San Antonio Rose' may be easily distinguished by the combination of green leaves and darker flowers of smaller size on 'Green Cloud', while 'San Antonio Rose' has silver/gray leaves, and much larger flowers which are lighter in color. Both cultivars have excellent resistance to damping off. 'Green Cloud' is a larger plant at maturity than 'San Antonio Rose'.

Compared to its male parent, 'Convent', 'San Antonio Rose' may be distinguished by the following characteristics. 'Convent' is a smaller plant, with whiter leaves and the reddest flowers of all the cultivated *Leucophyllums*. 'Convent' is highly susceptible to damping off in the nursery and is rarely seen in the trade. 'San Antonio Rose' has silver/gray leaves, pink flowers of larger size, a somewhat larger plant, and is highly resistant to damping off in the nursery.

Compared to the superficially similar cultivar, 'Compacta', 'San Antonio Rose' has flowers fully double the size of those of 'Compacta'. 'San Antonio Rose' also has improved resistance to damping off fungi compared to 'Compacta'.

Compared to 'White Cloud' (not patented), 'San Antonio Rose' is a smaller plant with colored flowers, compared to white flowers on 'White Cloud'.

Compared to 'Heavenly Cloud' (not patented) , an interspecies hybrid between *Leucophyllum frutescens* and *L. laevigatum*, 'San Antonio Rose' is a rounded shrub, while 'Heavenly Cloud' has a wider, somewhat sprawling form. Also 'Heavenly Cloud' has greener leaves than 'San Antonio Rose' and a different flower color. 'San Antonio Rose' also has larger flowers than 'Heavenly Cloud'.

We claim:

1. A new and distinct *Leucophyllum frutescens* plant substantially as described and illustrated herein.

* * * * *